(12) United States Patent
Carrillo

(10) Patent No.: US 12,714,451 B2
(45) Date of Patent: Aug. 25, 2026

(54) DEVICES, SYSTEMS, AND METHODS FOR RETRIEVAL OF MATERIAL FROM VESSEL LUMENS

(71) Applicant: Covidien LP, Mansfield, MA (US)

(72) Inventor: Ramon Carrillo, Santa Ana, CA (US)

(73) Assignee: Covidien LP, Mansfield, MA (US)

( * ) Notice: Subject to any disclaimer, the term of this patent is extended or adjusted under 35 U.S.C. 154(b) by 130 days.

(21) Appl. No.: 18/634,126

(22) Filed: Apr. 12, 2024

(65) Prior Publication Data

US 2024/0358385 A1 Oct. 31, 2024

Related U.S. Application Data

(60) Provisional application No. 63/499,192, filed on Apr. 28, 2023.

(51) Int. Cl.
*A61B 17/22* (2006.01)
*A61B 17/00* (2006.01)

(52) U.S. Cl.
CPC .................. *A61B 17/22031* (2013.01); *A61B 2017/00292* (2013.01); *A61B 2017/00358* (2013.01); *A61B 2017/00778* (2013.01)

(58) Field of Classification Search
CPC ........ A61B 2017/22079; A61B 17/221; A61B 17/22031; A61B 2017/00292; A61B 2017/00358; A61B 2017/00778; A61B 2017/2079; A61B 2017/2212; A61B 2017/2215; A61B 2017/2217; A61B 2017/22034; A61B 2017/220352; A61F 2/01; A61F 2/0103; A61F 2/0105; A61F 2/0108; A61F 2/013; A61F 2/014; A61F 2/015; A61F 2/018; A61F 2/848; A61F 2002/015; A61F 2002/016; A61F 2002/018; A61F 2002/8483; A61F 2002/8486
USPC ................................................ 606/127, 159
See application file for complete search history.

(56) References Cited

U.S. PATENT DOCUMENTS

| | | | | |
|---|---|---|---|---|
| 5,897,589 | A | 4/1999 | Cottenceau et al. | |
| 2002/0095161 | A1* | 7/2002 | Dhindsa | A61B 17/221 606/120 |
| 2010/0070024 | A1 | 3/2010 | Venturelli et al. | |
| 2010/0185230 | A1* | 7/2010 | Horan | A61F 2/01 606/200 |
| 2016/0270935 | A1 | 9/2016 | Rasmussen et al. | |

(Continued)

FOREIGN PATENT DOCUMENTS

EP 2298248 A1 3/2011

*Primary Examiner* — Kankindi Rwego
(74) *Attorney, Agent, or Firm* — Fortem IP LLP

(57) ABSTRACT

Devices, systems, and methods for retrieving clot material from a vessel lumen are disclosed herein. According to some embodiments, the present technology includes a clot retrieval device comprising a tubular mesh configured to transition between a low-profile state for delivery through a delivery catheter and an expanded state for deployment in a blood vessel at a treatment site proximate a clot. The device can include a webbing coupled to the tubular mesh and comprising a plurality of filaments coupled to and extending across a lumen of the mesh. When the device is in the expanded state within the blood vessel at the treatment site, the mesh is configured to engage peripheral portions of the clot and the webbing is configured to engage non-peripheral portions of the clot.

20 Claims, 10 Drawing Sheets

(56) References Cited

U.S. PATENT DOCUMENTS

| | | | | |
|---|---|---|---|---|
| 2019/0254691 | A1 | 8/2019 | Martin et al. | |
| 2022/0192688 | A1 * | 6/2022 | Olsen | A61B 90/39 |

* cited by examiner 200
204
202
220a
206
220
220b

660
CM
V 660
662
600
CM
V
664

DEVICES, SYSTEMS, AND METHODS FOR RETRIEVAL OF MATERIAL FROM VESSEL LUMENS

CROSS-REFERENCE TO RELATED APPLICATIONS

This application claims the benefit of and priority to U.S. Provisional Patent Application Ser. No. 63/499,192 filed Apr. 28, 2023, the entire disclosure of which is incorporated by reference herein.

TECHNICAL FIELD

The present technology relates generally to devices and methods for removing obstructions from body lumens. Some embodiments of the present technology relate to devices and methods for removal of clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increase the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages using this approach.

For example, one disadvantage is that the stent may not sufficiently retain the clot as it pulls the clot to the catheter. In such a case, some or all of the clot might remain the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessel.

SUMMARY

The present technology relates generally to devices and methods for removing obstructions from body lumens. Some embodiments of the present technology relate to devices and methods for removal of clot material from blood vessels. The subject technology is illustrated, for example, according to various aspects described below, including with reference to FIGS. 1-6C. Various examples of aspects of the subject technology are described as numbered clauses (1, 2, 3, etc.) for convenience. These are provided as examples and do not limit the subject technology.

Example 1: A clot retrieval device for removing a clot from a blood vessel, the device comprising: a tubular scaffold comprising a plurality of struts interconnected at apices and defining a plurality of open cells, wherein: the scaffold is configured to transition between a delivery state and an expanded state, in the delivery state the scaffold defines a first diameter around the longitudinal axis of the tubular scaffold, and in the expanded state the scaffold defines a lumen and a second diameter around the longitudinal axis of the tubular scaffold, larger than the first diameter, and a webbing assembly coupled to the tubular scaffold and comprising a plurality of filaments coupled to the plurality of struts or apices, or both, wherein: in the expanded state, each of the filaments span the lumen, and the scaffold and the webbing assembly are configured to be advanced distally in the delivery state within a catheter through the clot, deployed distal of the clot out an end of the catheter allowing the scaffold to transition from the delivery state toward the expanded state, and with the scaffold in the expanded state withdrawn proximally to remove the clot by both: engagement of peripheral portions of the clot, positioned within the open cells, with the plurality of struts and apices and engagement of central portions of the clot, positioned within the lumen, with the webbing assembly.

Example 2: The clot retrieval device of Example 1, wherein the one or more filaments define a plurality of segments, and wherein in the expanded state each segment extends from the plurality of struts or apices into the lumen.

Example 3: The clot retrieval device of Example 2, wherein the plurality of filaments comprises a first filament and a second filament, and wherein, in the expanded state, the first filament and the second filament cross in a projection onto a plane perpendicular to the longitudinal axis.

Example 4: The clot retrieval device of Example 3, wherein the first filament and the second filament are in contact at a location within the lumen in the expanded state.

Example 5: The clot retrieval device of any one of Clauses 1 to 4, wherein at least one of the plurality of filaments is not perpendicular to the longitudinal axis of the tubular scaffold in the expanded state.

Example 6: The clot retrieval device of any one of Examples 1 to 5, wherein the plurality of filaments comprise different segments of a single, continuous filament.

Example 7: The clot retrieval device of any one of Examples 1 to 5, wherein the plurality of filaments comprise separate, discrete filaments.

Example 8: The clot retrieval device of any one of Examples 1 to 7, wherein the webbing assembly is a first webbing assembly and the plurality of filaments is a plurality of first filaments, and wherein the clot retrieval device further comprises a second webbing assembly coupled to the tubular scaffold and longitudinally offset from the first webbing assembly, the second webbing assembly comprising a plurality of second filaments coupled to the plurality of struts or apices, or both, and wherein: in the expanded state, the plurality of second filaments span the lumen, and the scaffold, the first webbing assembly, and the second webbing assembly are configured to be advanced distally in the delivery state within a catheter through the clot, deployed distal of the clot out an end of the catheter allowing the scaffold to transition from the delivery state toward the expanded state, and with the scaffold in the expanded state withdrawn proximally, to remove the clot by engagement of peripheral portions of the clot, positioned within the open cells, with the plurality of struts and apices and engagement of central portions of the clot, positioned within the lumen, with the first webbing assembly and the second webbing assembly.

Example 9: The clot retrieval device of Example 8, wherein a distance of the longitudinal offset between the first and second webbing assemblies is at least one third of a length of the scaffold.

Example 10: The clot retrieval device of any one of Examples 1 to 9, wherein each of the plurality of filaments extends between respective ends, and wherein each of the ends of the plurality of filaments are coupled to one of the struts or one or the apices.

Example 11: The clot retrieval device of Example 10, wherein at least one of the ends of the plurality of filaments is coupled to the one of the struts or the one of the apices with an adhesive.

Example 12: The clot retrieval device of Example 10, wherein at least one of the ends of the plurality of filaments is coupled to the one of the struts or the one of the apices with a knot.

Example 13: The clot retrieval device of Example 1, wherein a molded monolithic body defines the plurality of filaments.

Example 14: The clot retrieval device of any one of the previous Examples, wherein the plurality of filaments define an hourglass shape.

Example 15: The clot retrieval device of any one of the previous Examples, wherein the plurality of filaments are in slack with the scaffold is in the expanded state.

Example 16: The clot retrieval device of any one of the previous Examples, wherein: each of the plurality of filaments extends between respective first and second ends and has a length measured along the respective filament between the first and second ends, each of the first and second ends of the plurality of filaments are coupled to the scaffold at corresponding first and second locations, the first and second locations being separated by a distance measured directly across the lumen of the scaffold when the scaffold is in the expanded state, and the length of each of the filaments is at least 10% longer than the distance between the first and second locations.

Example 17: A clot retrieval device for removing a clot from a blood vessel, the device comprising: a tubular mesh configured to transition between a low-profile state for delivery through a delivery catheter and an expanded state for deployment in the blood vessel at a treatment site proximate a clot, and a webbing coupled to the tubular mesh and comprising a plurality of filaments, each extending between corresponding first and second ends, wherein the first and second ends are coupled to the mesh at different locations, and wherein, in the expanded state, each of the filaments span the lumen, the device is configured to be expanded within the blood vessel at the treatment site, and wherein the mesh is configured to engage peripheral portions of the clot and the webbing is configured to engage non-peripheral portions of the clot.

Example 18: The clot retrieval device of Example 17, wherein the one or more filaments define a plurality of segments, and wherein in the expanded state each segment extends from the plurality of struts or apices into the lumen.

Example 19: The clot retrieval device of Example 17 or Example 18, wherein the plurality of filaments comprises a first filament and a second filament, and wherein, in the expanded state, the first filament and the second filament cross in a projection onto a plane perpendicular to the longitudinal axis.

Example 20: The clot retrieval device of Clause 19, wherein the first filament and the second filament are in contact at a location within the lumen in the expanded state.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments in addition to those described herein are within the scope of the technology. For example, the retrieval devices of the present technology may be used to remove emboli from body lumens other than blood vessels (e.g., the digestive tract, etc.) and/or may be used to remove emboli from blood vessels outside of the brain (e.g., pulmonary blood vessels, blood vessels within the legs, etc.). In addition, the retrieval devices of the present technology may be used to remove luminal obstructions other than clot material (e.g., plaque, resected tissue, foreign material, etc.).

Figure 1:
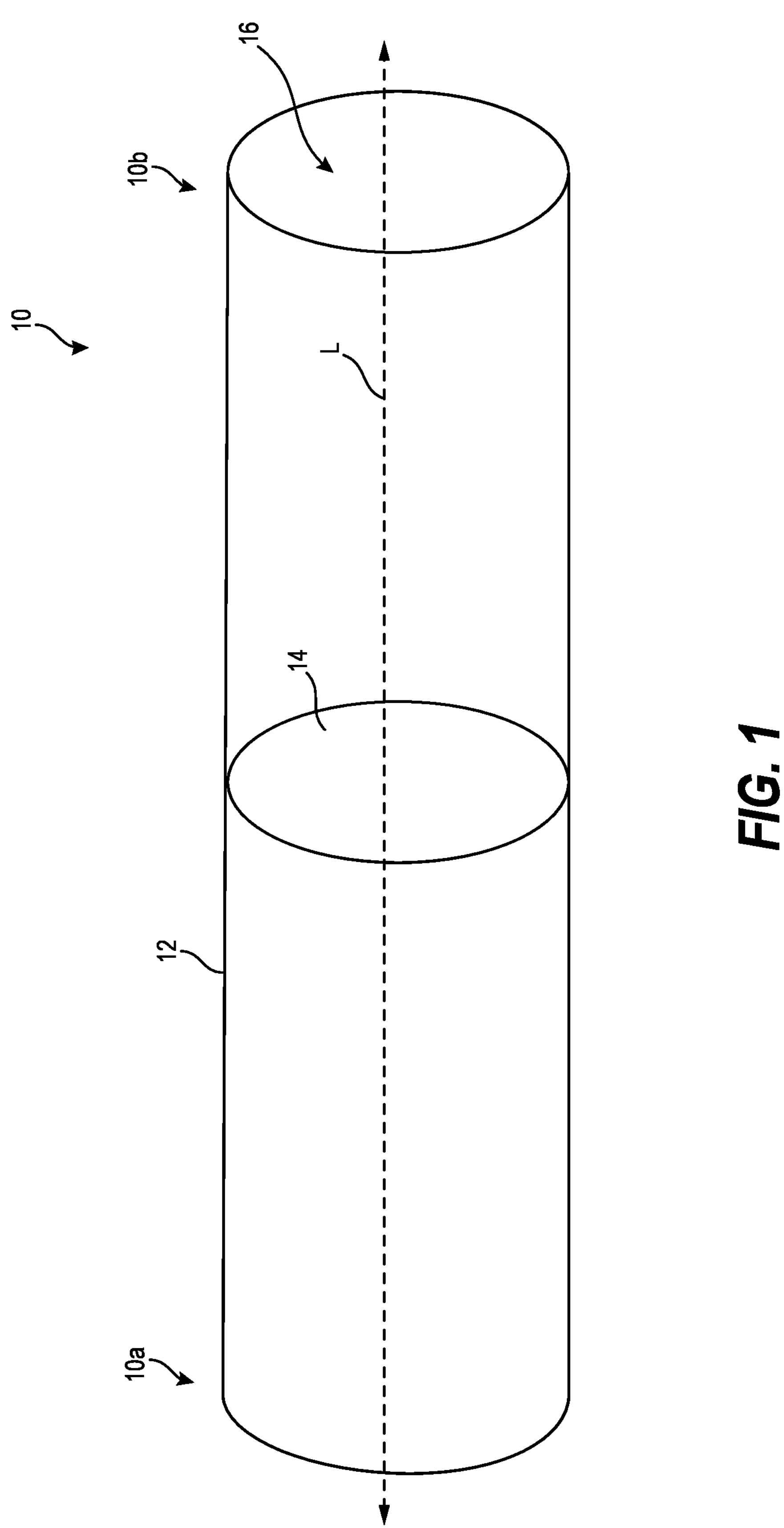
FIG. 1 is a perspective view of a clot retrieval device in accordance with several embodiments of the present technology.

A clot retrieval device 10 (or "device 10") configured in accordance with several embodiments of the present technology is shown in FIG. 1. As shown, the clot retrieval device 100 can comprise a tubular structure 12 and a webbing assembly 14 (shown schematically) coupled to the tubular scaffold 12. The device 10 has a proximal portion 10*a* configured to be permanently coupled to an elongate delivery member (not shown), a distal portion 10*b*, and a longitudinal axis L extending between the proximal and distal portions 10*a*, 10*b*. The device 10 further comprises a lumen 106 defined by an inner surface of the scaffold 12. The device 10 can have a low-profile delivery configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel.

The tubular structure 12 can be formed of a superelastic material (e.g., Nitinol, a cobalt-chromium alloy, etc.) or other resilient material configured to self-expand when the tubular structure 12 is released from a delivery catheter. In some embodiments the tubular structure 12 has a substantially constant outer diameter, and in some embodiments the tubular structure 12 has a varying outer diameter.

The webbing assembly 14 can comprise a porous structure extending across a lumen 16 of the device 10. The webbing assembly 14 beneficially provides additional surface area within the device lumen 16 for engaging clot material and/or preventing distal movement of the clot material within the lumen 16 during withdrawal of the device 10 and enmeshed clot material from the body. The webbing assembly 14 can be sufficiently flexible to accommodate both the compressed delivery configuration of the tubular structure 12 and the expanded configuration. In addition, the webbing assembly 14 can be configured such that it does not exert a radially compressive force on the tubular structure 12 and impede expansion.

Any of the tubular structures described below can be used with the device 10 of FIG. 1. Likewise, any of the webbing assemblies described below can be used with the device 10 of FIG. 1.

Figure 1A:
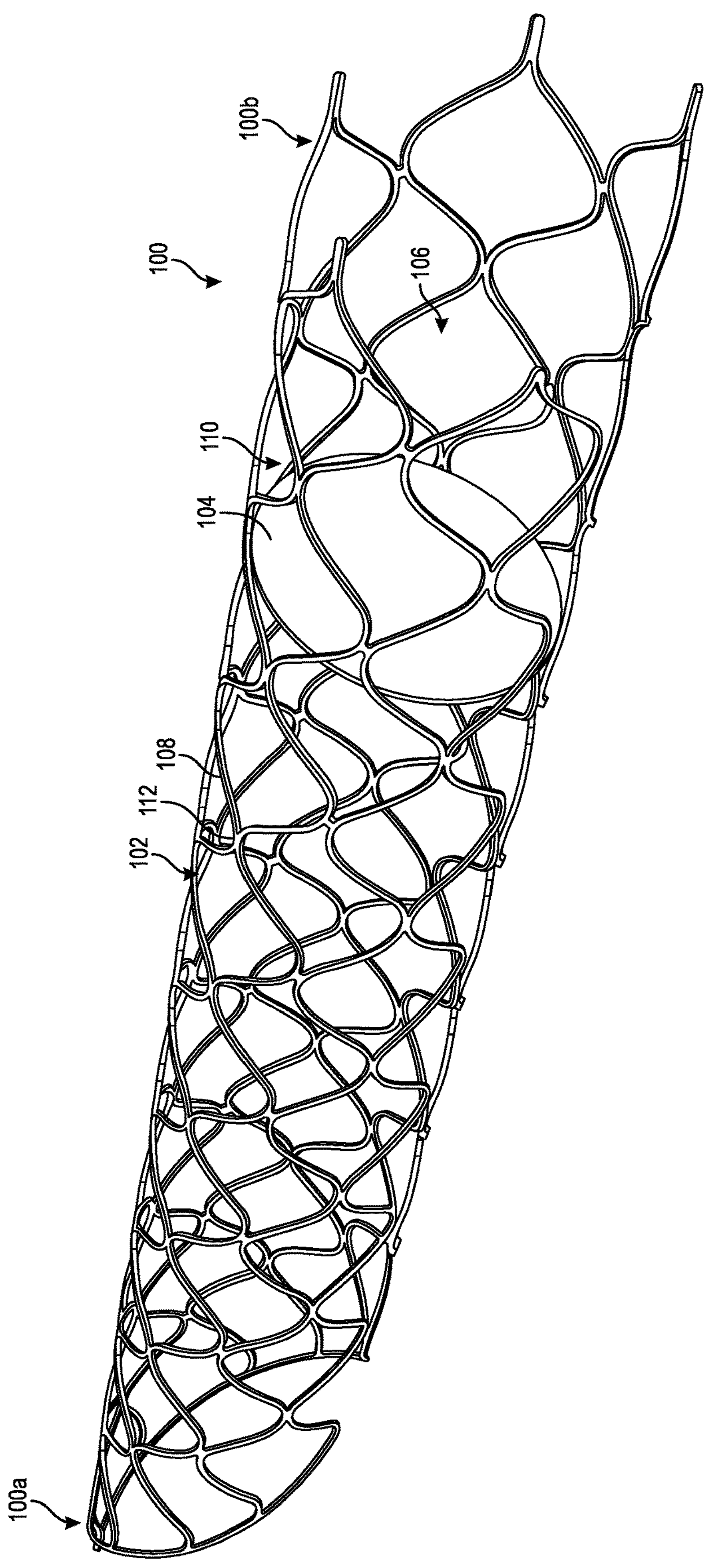
FIGS. 1A and 1B are perspective and side views, respectively, of a clot retrieval device in accordance with several embodiments of the present technology.
Figure 1B:
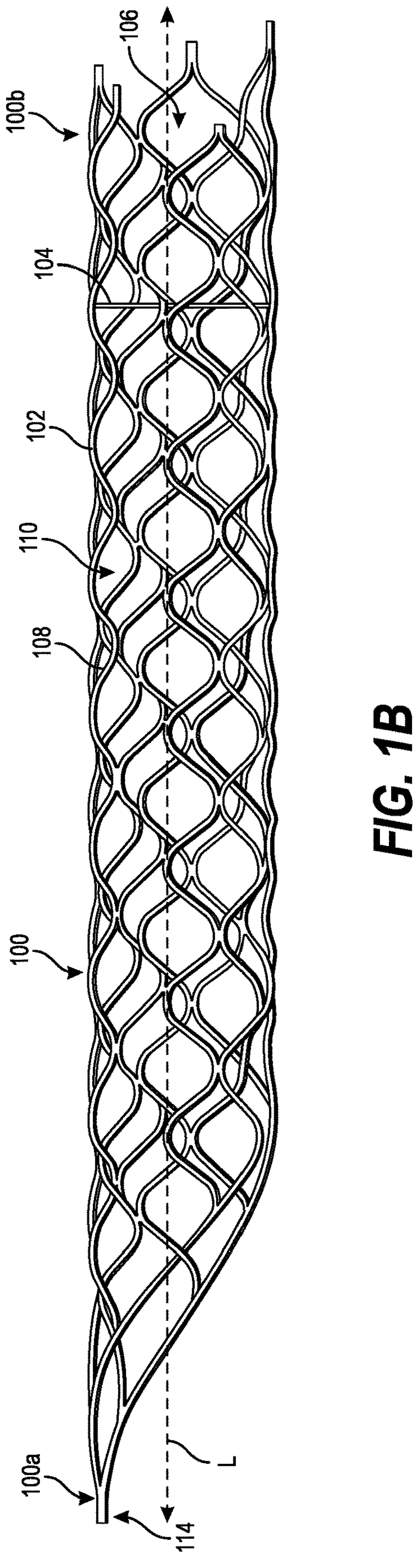

A clot retrieval device 100 (or "device 100") configured in accordance with several embodiments of the present technology is shown in FIGS. 1A and 1B. As shown, the clot retrieval device 100 can comprise a tubular scaffold 102 and a webbing assembly 104 (shown schematically) coupled to the tubular scaffold 102. The device 100 has a proximal portion 100*a* configured to be permanently coupled to an elongate delivery member (not shown), a distal portion 100*b*, and a longitudinal axis L (see FIG. 1B) extending between the proximal and distal portions 100*a*, 100*b*. The device 100 further comprises a lumen 106 defined by an inner surface of the scaffold 102. The device 100 can have a low-profile delivery configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel.

The scaffold 102 can comprise a plurality of struts 108 interconnected at apices 112 and together defining a plurality of open cells 110. In some embodiments, the distal portion 100*b* of the device 100 can be generally tubular (e.g., cylindrical), and the proximal portion 100*a* of the device 100 can taper proximally to a coupling region 114 (best visualized in FIG. 1B). In other embodiments, the device 100 can take any number of shapes or forms. The scaffold 102 can be formed of a superelastic material (e.g., Nitinol, a cobalt-chromium alloy, etc.) or other resilient material configured to self-expand when the scaffold 102 is released from a delivery catheter.

The webbing assembly 104 can comprise one or more filaments (not shown in FIGS. 1A and 1B) coupled to the scaffold 102 and extending across the lumen 106 of the device 100. The webbing assembly 104 beneficially provides additional surface area within the device lumen 106 for engaging clot material and/or preventing distal movement of the clot material within the lumen 106 during withdrawal of the device 100 and enmeshed clot material from the body. The filaments can be sufficiently flexible to accommodate both the compressed delivery configuration of the scaffold 102 and the expanded configuration. In addition, the filaments can be configured such that the filaments do not exert a radially compressive force on the scaffold 102 and impede expansion. For example, the filaments can have a length that is the same as or greater than a diameter of the lumen 106. In some embodiments, the filaments are in slack (e.g., not in tension) when the scaffold 102 is in the expanded configuration.

In certain embodiments, the filaments may be comprised of polymeric materials. The polymeric materials can be nonbiodegradable polymers such as polyethylene, polyacrylics, polypropylene, polyvinylchloride, polyamides such as nylon, e.g., Nylon 6.6, polyurethanes, polyvinylpyrrolidone, polyvinyl alcohols, polyvinylacetate, cellulose acetate, polystyrene, polytetrafluoroethylene, polyesters such as polyethylene terephthalate (Dacron), silk, cotton, and the like. In certain specific embodiments the nonbiodegradable materials for the polymer component may comprise polyesters, polyethers, polyamides and polyfluorocarbons. The polymers can be biodegradable as well. Representative biodegradable polymers include: polyglycolic acid/polylactic acid (PGLA), polycaprolactone (PCL), polyhydroxybutyrate valerate (PHBV), polyorthoester (POE), polyethyleneoxide/polybutylene terephthalate (PEO/PBTP), polylactic acid (PLA), polyglycolic acid (PGA), poly (p-dioxanone), poly (valerolactone), poly (tartronic acid), poly (beta malonic acid), poly (propylene fumarate), poly (anhydrides); and tyrosine-based polycarbonates.

In some embodiments, a molded monolithic body defines the plurality of filaments. For example, the plurality of filaments can be portions of a web comprising a central apex and arms extending radially away from the apex, where the apex and arms comprise a single molded piece. In such embodiments, the monolithic body can comprise a flexible and/or elastic material, such as any of the polymeric materials listed above.

Within a given webbing assembly, the filaments can have various arrangements, as detailed below in FIGS. 2A-2D. The features of the scaffold 202 in FIGS. 2A-2D can be generally similar to the features of the scaffold 102 of FIGS. 1A and 1B, or the tubular structure 12 in FIG. 1. Accordingly, like numbers (e.g., strut 108 versus strut 208) are used to identify similar or identical components in FIGS. 1-2D.

Figure 2A:
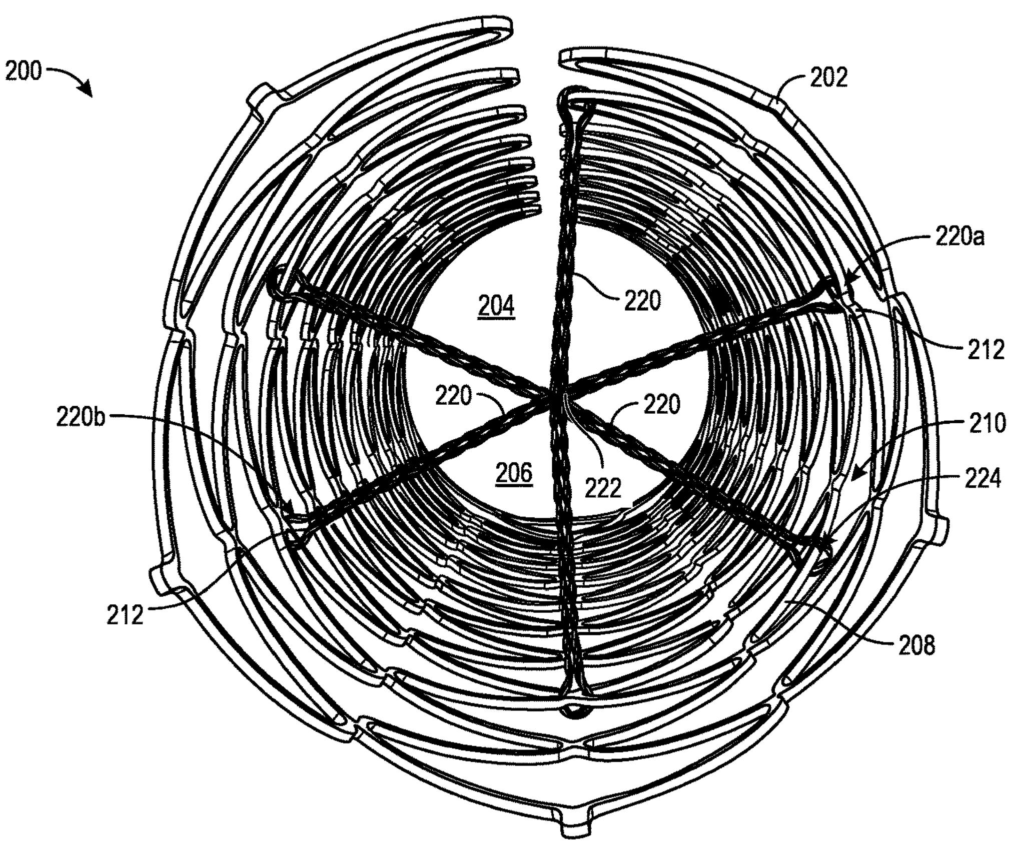
FIGS. 2A, 2B, 2C, and 2D are axial views showing different webbing assembly configurations of a clot retrieval device in accordance with several embodiments of the present technology.
Figure 2B:
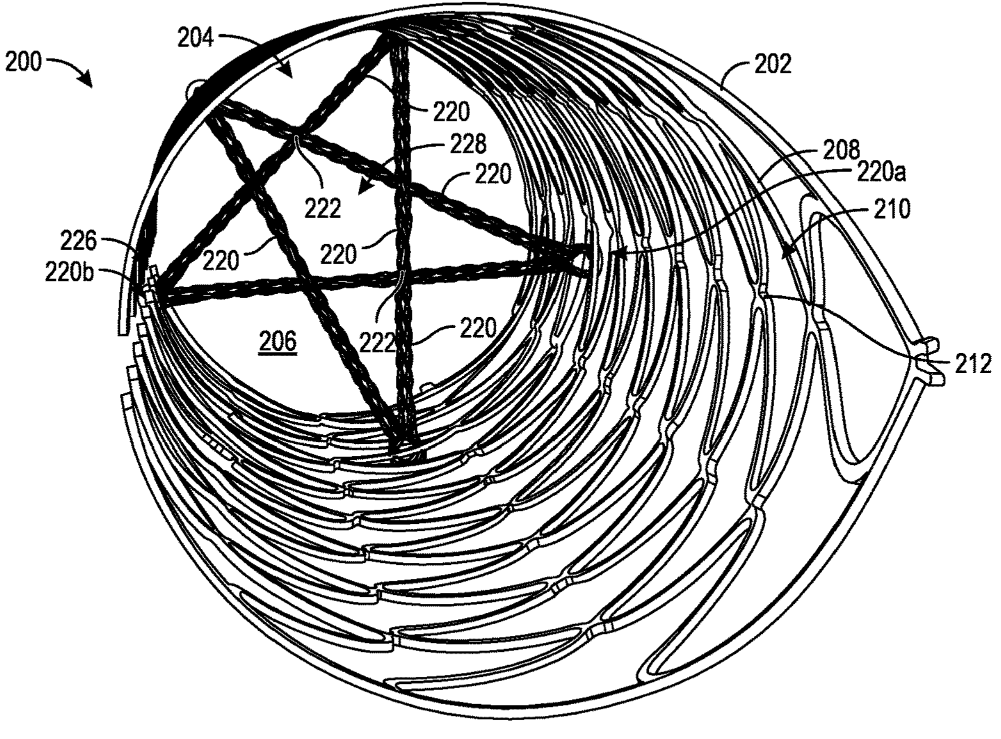

FIG. 2A is an axial view of a device 200 comprising a scaffold 202 and a webbing assembly 204. The webbing assembly 204 can comprise a plurality of filaments 220, each extending across the lumen 206 of the scaffold 202. Each of the filaments 220 can have a first end 220*a* (only labeled for one of the filaments), a second end 220*b*, and a length extending therebetween. The filaments 220 can be separate, discrete filaments (as shown in FIG. 2A), or may be different portions of a single continuous filament (as shown in FIG. 2B). A single webbing assembly 204 can comprise only separate, discrete filaments, only a single continuous filament, or a mixture of both. While the webbing assembly 204 of FIG. 2A comprises three filaments 220, in other embodiments the webbing assembly 204 can comprise more or fewer filaments 220, such as one filament, two filaments, four filaments, five filaments, six filaments, seven filaments, eight filaments, etc.

As shown in FIG. 2A, the first and second ends 220*a*, 220*b* of each of the filaments 220 are coupled to one of the struts 208 or one or the apices 212. For those filaments 220 that comprise a single, discrete filament (as in FIG. 2A), the first and second ends 220*a*, 220*b* can define an opening 224, and the strut 208 or apex 212 is positioned within the opening 224. The opening 224 may be large enough to accommodate movement of the first and second ends 220*a*, 220*b* relative to the scaffold 202 (within the confines of the cell 210 in which the first or second end 220*a*, 220*b* is positioned), or the opening 224 may be tightly fit to the strut 208 or apex 212 such that the first or second end 220*a*, 220*b* is substantially fixed in place. In some embodiments, the opening 224 is formed by a knot at the respective first or second end 220*a*, 220*b*. Additionally or alternatively, the first and second ends 220*a*, 220*b* can be coupled to the strut 208 or apex 212 with an adhesive. For those filaments 220 that are portions of a single continuous filament (as in FIG. 2B), the first and second ends 220*a*, 220*b* can be looped around a strut 208 or apex 212. The looped portions 226 can remain free to slide along the strut 208 or apex 212 (within the confines of the cell 210 in which the first or second end 220*a*, 220*b* is positioned), or may be fixed in place (for example, via an adhesive).

Figures 2C, 2D:
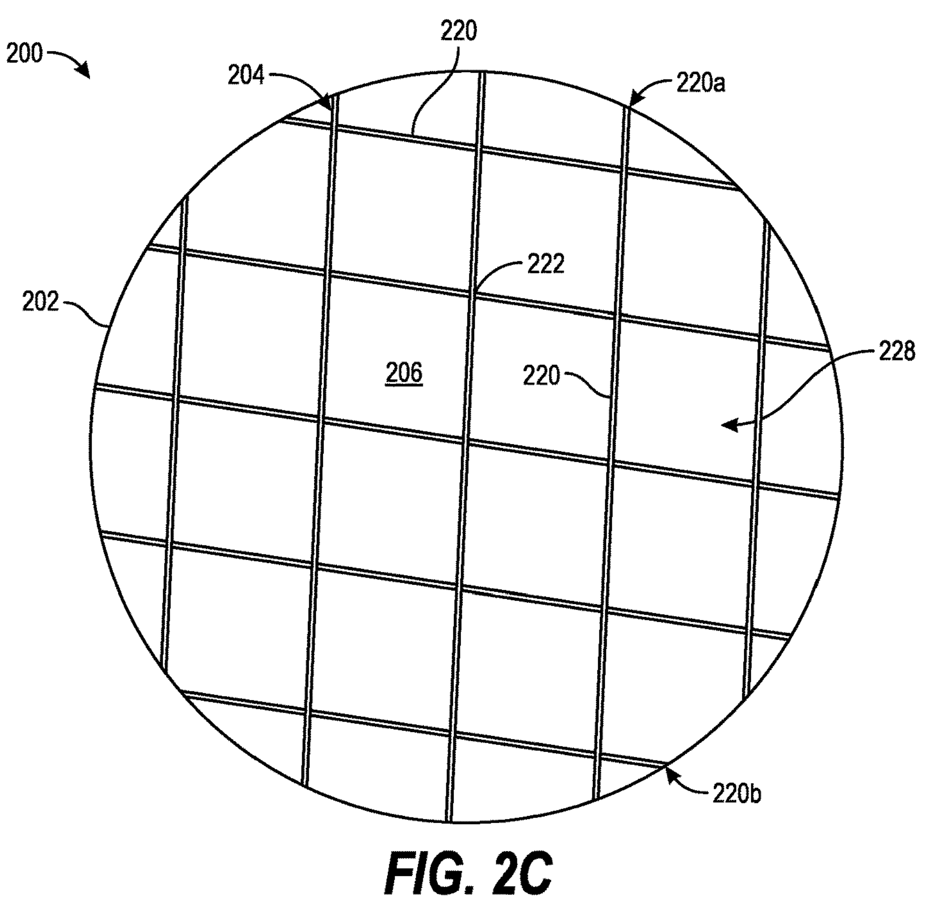

The first and second ends 220*a*, 220*b* of the filaments 220 can be coupled to the scaffold 202 at locations that are diametrically opposed such that the filaments 220 cross one another at a single point 222 (as shown in FIG. 2A) that located at a center of the lumen 206. In some embodiments, the first and second ends 220*a*, 220*b* of at least one of the filaments 220 are coupled to the scaffold 202 at locations that are not diametrically opposed such that the webbing assembly 204 includes multiple crossing points 222 (as shown in FIGS. 2B and 2C) and cells 228 completely enclosed by the filaments 220. In several of such configurations, the filaments 220 can be arranged in a star (FIG. 2B), a grid (FIG. 2C), or other configurations. At any of the crossing points 222, the filaments 220 may or may not contact one another. In certain embodiments, the filaments 220 are coupled to one another at the crossing points. For example, the filaments 220 can be coupled to one another via an adhesive, a tie, etc., may be threaded through one another (as shown in FIG. 2A), may be wrapped around one another, and/or other means for adhering. In some variations, the filaments 220 do not cross (as shown in FIG. 2D).

Figure 3A:
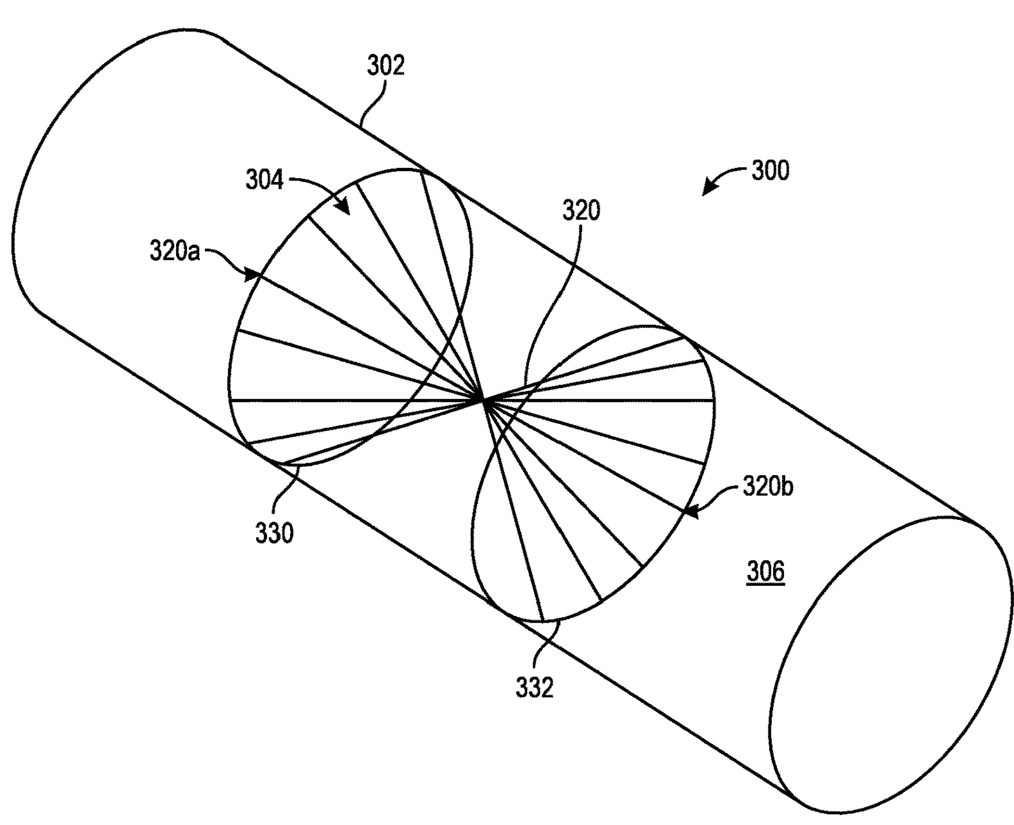
FIGS. 3A and 3B are perspective and side views, respectively, of a clot retrieval device (shown schematically) with a longitudinally extending webbing in accordance with several embodiments of the present technology.
Figure 3B:
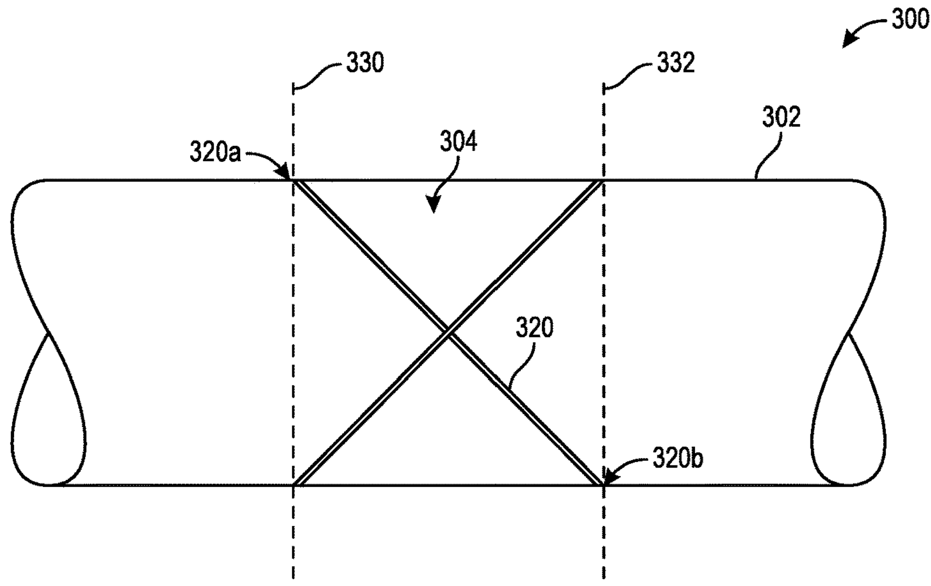

Referring still to FIG. 2A, some or all of the filaments 220 may extend across the lumen 206 at substantially the same location along the longitudinal axis L (see FIG. 1B) of the scaffold 202 such that such filaments 220 lie substantially within a single plane that is perpendicular to the longitudinal axis L. In some embodiments, for example as shown in FIGS. 3A and 3B, one, some, or all of the filaments 320 may have a first end 320*a* at a first location along the longitudinal axis L and a second end 320*b* at a second location along the longitudinal axis L spaced apart from the first location such that the respective filament 320 extends a length along the longitudinal axis L as it crosses the lumen 306. In several of such embodiments, the first ends 320*a* of the filaments 320 may be disposed at a first longitudinal location and/or substantially within a first plane 330 along the longitudinal axis L and the second ends 320*b* may be disposed at a second longitudinal location and/or substantially within a second plane 332 along the longitudinal axis L. In such embodiments, the filaments 320 may cross at a single point 322 such that the webbing assembly 304 has an hourglass shape, as shown in FIGS. 3A and 3B. In other embodiments, the first and second ends 320*a*, 320*b* of the filaments 320 may be staggered (e.g., not aligned).

Figure 4:
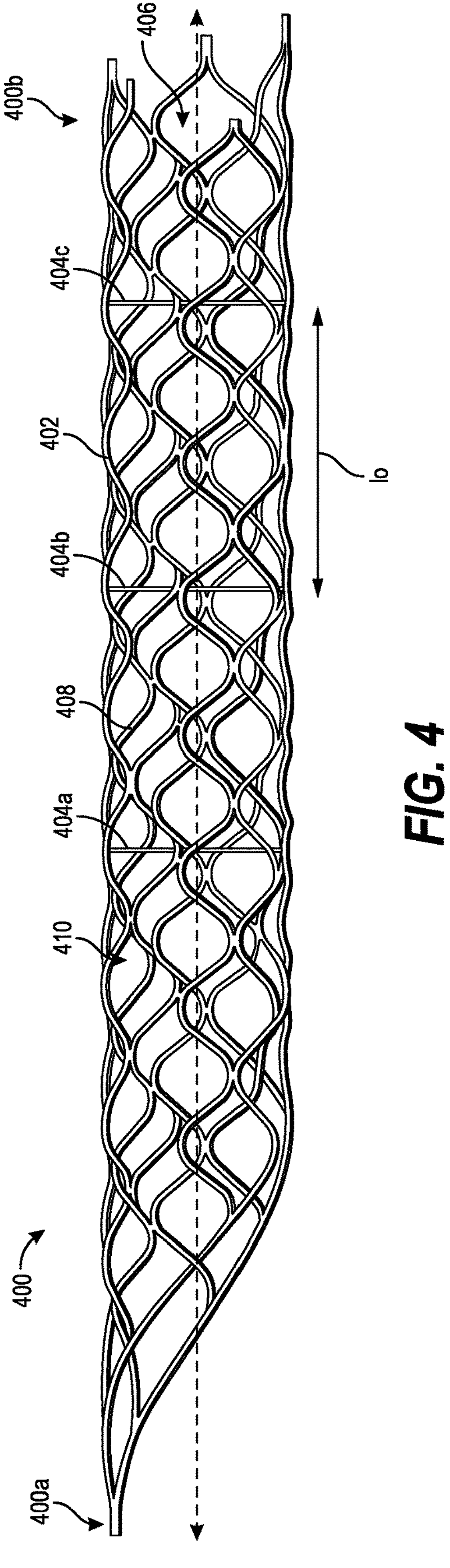
FIG. 4 is a side view of a clot retrieval device having a plurality of discrete webbing assemblies in accordance with several embodiments of the present technology.

FIG. 4 shows a device 400 configured in accordance with several embodiments of the present technology in which the device 400 includes multiple webbing assemblies 404*a*, 404*b*, 404*c* spaced apart from one another along the longitudinal axis L of the scaffold 402. A distance of the longitudinal offset lo between longitudinally adjacent webbing assemblies can be at least one third of a length of the scaffold. While the device 400 in FIG. 4 comprises three webbing assemblies 404*a*, 404*b*, 404*c*, in other embodiments the device 400 can comprise more or fewer webbing assemblies, such as one webbing assembly, two webbing assemblies, four webbing assemblies, five webbing assemblies, six webbing assemblies, seven webbing assemblies, eight webbing assemblies, etc. When more than two webbing assemblies are utilized, longitudinally adjacent webbing assemblies can be separated by the same or different lengths. The different assemblies 404*a*, 404*b*, 404*c* can have the same or different filament arrangements. Moreover, the different assemblies 404*a*, 404*b*, 404*c* can comprise any of the filament arrangements disclosed herein, including with reference to FIGS. 2A-3B. In some embodiments comprising multiple webbing assemblies, it may be beneficial for the different webbing assemblies to have different properties. For example, the device 400 can have a distal webbing assembly (at the distal end of spaced apart from the distal end of the device 400) and a proximal webbing assembly (at the proximal end or spaced apart from the proximal end of the device 400, where the distal webbing assembly can be less porous and/or less flexible so as to better capture distally traveling clot material during withdrawal. For example, the distal webbing assembly can have more filaments (and less total space between filaments), may include more filaments, may include filaments having a smaller diameter, etc.

Figure 5A:
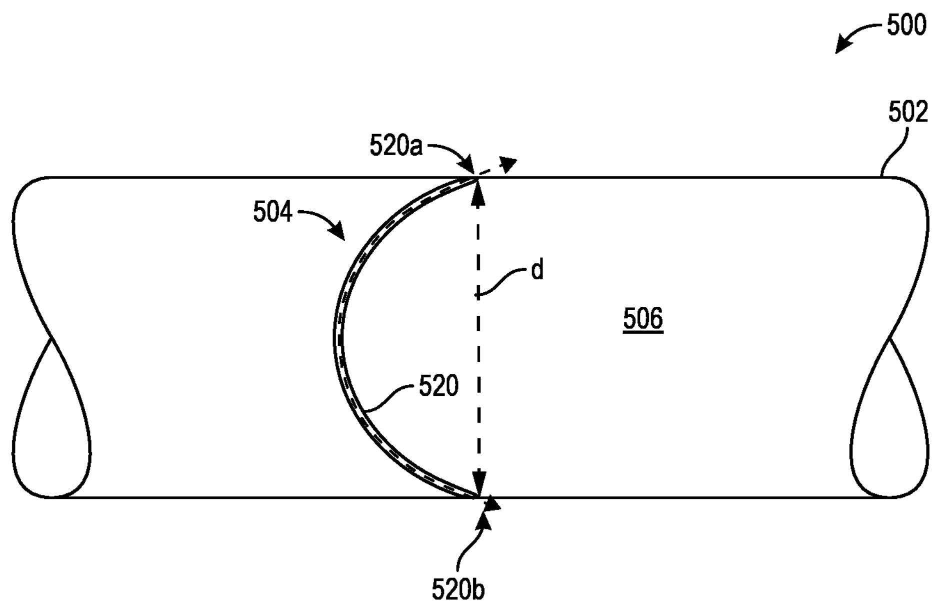
FIG. 5A is a side view of a portion of a clot retrieval device (shown schematically), showing a webbing in slack, in accordance with several embodiments of the present technology.
Figure 5B:
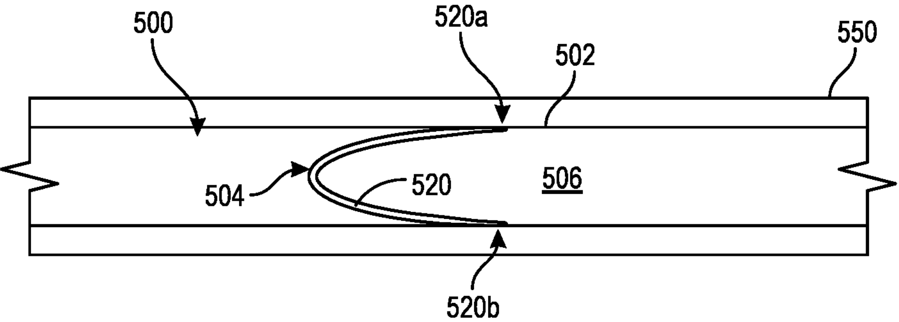
FIG. 5B is a side view of a clot retrieval device (shown schematically) in a compressed state within a catheter, in accordance with several embodiments of the present technology.

As previously mentioned, the filaments of the webbing assemblies of the present disclosure can be sufficiently flexible to accommodate both the compressed delivery configuration of the scaffold and the expanded configuration. In addition, the filaments can be configured such that the filaments do not exert a radially compressive force on the scaffold 102 and impede expansion. FIG. 5A, for example, schematically depicts a device 500 of the present technology in the expanded configuration with the filaments 520 of the webbing assembly 504 in slack (e.g., not in tension). In some cases, a length of the individual filaments 520 (measured along a longitudinal axis L of the filaments 520 between respective first and second ends 520*a*, 520*b*) is at least 10% longer than a distance d (labeled in FIG. 5A) between the locations on scaffold 520, where the distance is measured in a straight line between the locations, across the lumen 506. FIG. 5B depicts the device 500 in a compressed or delivery configuration within a delivery catheter 550. As shown, the filaments 520 have additional slack and folded over within the lumen 506 of the scaffold 502. As the scaffold 502 transitions from the delivery configuration to the expanded configuration, a distance between the first and second ends 520*a*, 520*b* of the individual filaments increases, but without adding tension across the diameter of the scaffold 502.

Figures 6A, 6B:
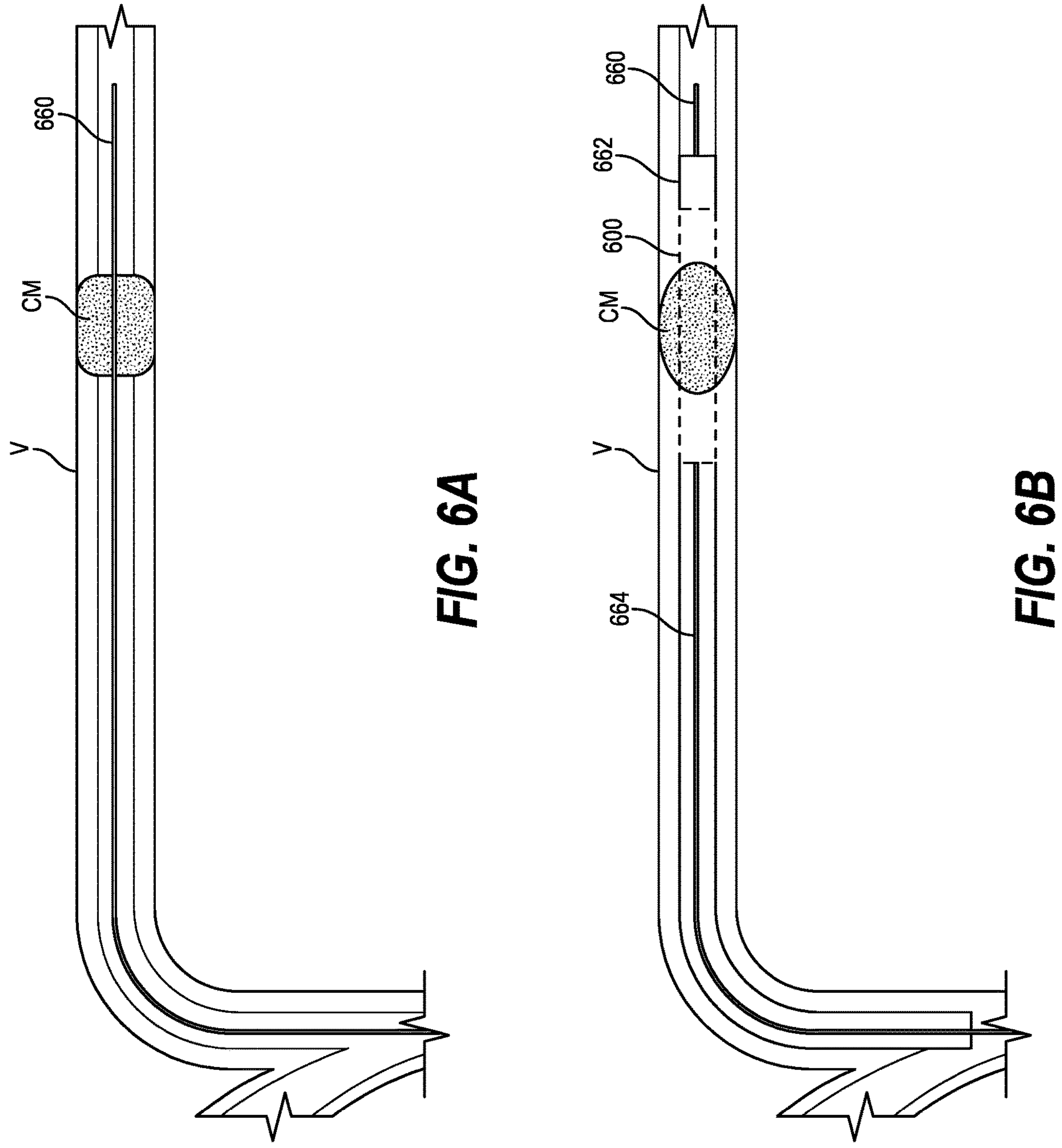
FIGS. 6A-6C show a method for retrieving clot material from a vessel lumen using the clot retrieval device of the present technology.
Figure 6C:
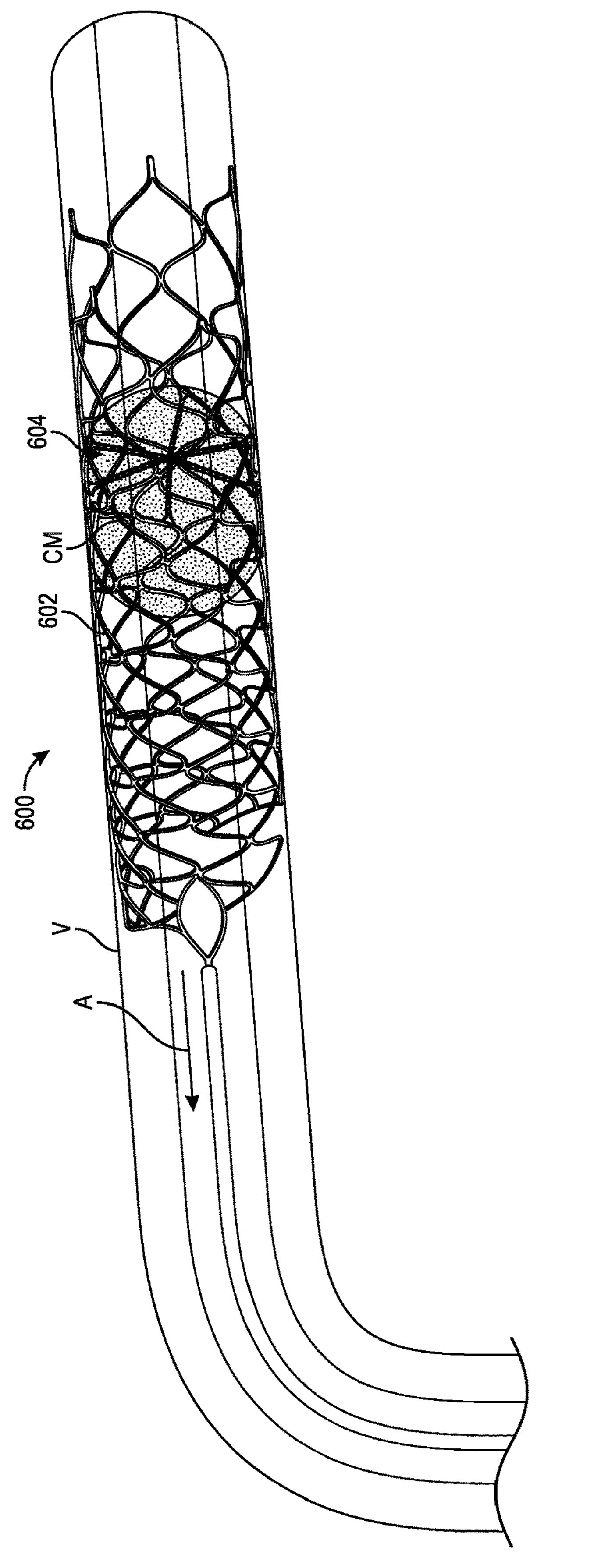

FIGS. 6A-6C depict a method of using a clot retrieval device 600 of the present technology. As shown in FIG. 6A, a guidewire 660 can be advanced through the vasculature V (such as the cerebral vascular) to a treatment site proximal clot material CM. The guidewire 660 can be advanced through the clot material CM. As shown in FIG. 6B, a delivery catheter 662 (e.g., a microcatheter) can then be advanced over the guidewire 660 and through the clot material CM. The delivery catheter 662 can contain the device 600 (shown schematically) in a delivery state. The proximal end of the device 600 is permanently coupled to an elongate delivery member 664 that extends back to an extracorporeal location. As shown in FIG. 6C, the catheter 662 can be withdrawn proximally of a proximal end of the device 600 such that the scaffold 602 is released from the constraints of the catheter 662 and allowed to self-expand within the clot material CM. The plurality of struts and apices of the scaffold 602 may engage peripheral portions of the clot material CM such that the clot material CM is positioned within at least some of the open cells of the scaffold 602, and the webbing assembly 604 may engage the central portions of the clot material CM. In some embodiments, the delivery catheter 662 is positioned such that deployment/expansion of the device 600 occurs distal of the clot material CM. In such embodiments, the device 600 can be pulled proximally (e.g., via the elongate member 664) to engage the clot material CM. Once the clot material CM is sufficiently enmeshed with the device 600, the device 600 and clot material CM can be withdrawn from the vasculature V (as indicated by arrow A in FIG. 6C).

CONCLUSION

Although many of the embodiments are described above with respect to devices, systems, and methods for mechanical thrombectomy, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-6C.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A clot retrieval device for removing a clot from a blood vessel, the device comprising:

a tubular scaffold comprising a plurality of struts interconnected at apices and defining a plurality of open cells, wherein:

the scaffold is configured to transition between a delivery state and an expanded state, in the delivery state the scaffold defines a first diameter around the longitudinal axis of the tubular scaffold, and in the expanded state the scaffold defines a lumen and a second diameter around the longitudinal axis of the tubular scaffold, larger than the first diameter, and a webbing assembly coupled to the tubular scaffold and comprising a plurality of filaments, each filament of the plurality of filaments extending between respective ends, wherein each of the ends is coupled to one of the plurality of struts or one of the apices, or both, wherein:

in the expanded state, each of the filaments span the lumen, wherein the ends of the filaments lie at a same axial location along the longitudinal axis, and the scaffold and the webbing assembly are configured to be advanced distally in the delivery state within a catheter through the clot, deployed distal of the clot out an end of the catheter allowing the scaffold to transition from the delivery state toward the expanded state, and with the scaffold in the expanded state withdrawn proximally to remove the clot by both:

engagement of peripheral portions of the clot, positioned within the open cells, with the plurality of struts and apices and engagement of central portions of the clot, positioned within the lumen, with the webbing assembly.

2. The clot retrieval device of claim 1, wherein the one or more filaments define a plurality of segments, and wherein in the expanded state each segment extends from the plurality of struts or apices into the lumen.

3. The clot retrieval device of claim 2, wherein the plurality of filaments comprises a first filament and a second filament, and wherein, in the expanded state, the first filament and the second filament cross in a projection onto a plane perpendicular to the longitudinal axis.

4. The clot retrieval device of claim 3, wherein the first filament and the second filament are in contact at a location within the lumen in the expanded state.

5. The clot retrieval device of claim 1, wherein at least one of the plurality of filaments is not perpendicular to the longitudinal axis of the tubular scaffold in the expanded state.

6. The clot retrieval device of claim 1, wherein the plurality of filaments comprise different segments of a single, continuous filament.

7. The clot retrieval device of claim 1, wherein the plurality of filaments comprise separate, discrete filaments.

8. The clot retrieval device of claim 1, wherein the webbing assembly is a first webbing assembly, the plurality of filaments is a plurality of first filaments, and the axial location is a first axial location, and wherein the clot retrieval device further comprises a second webbing assembly coupled to the tubular scaffold and longitudinally offset from the first webbing assembly, the second webbing assembly comprising a plurality of second filaments, each second filament of the plurality of second filaments extending between respective ends, wherein each of the ends of the second filaments is coupled to one of the plurality of struts or one of the apices, or both, and wherein:

in the expanded state, the plurality of second filaments span the lumen, wherein the ends of the second filaments lie at a same second axial location along the longitudinal axis, wherein the second axial location is different from the first axial location, and the scaffold, the first webbing assembly, and the second webbing assembly are configured to be advanced distally in the delivery state within a catheter through the clot, deployed distal of the clot out an end of the catheter allowing the scaffold to transition from the delivery state toward the expanded state, and with the scaffold in the expanded state withdrawn proximally, to remove the clot by engagement of peripheral portions of the clot, positioned within the open cells, with the plurality of struts and apices and engagement of central portions of the clot, positioned within the lumen, with the first webbing assembly and the second webbing assembly.

9. The clot retrieval device of claim 8, wherein a distance of the longitudinal offset between the first and second webbing assemblies is at least one third of a length of the scaffold.

10. The clot retrieval device of claim 1, wherein at least one of the ends of the plurality of filaments is coupled to the one of the struts or the one of the apices with an adhesive.

11. The clot retrieval device of claim 1, wherein at least one of the ends of the plurality of filaments is coupled to the one of the struts or the one of the apices with a knot.

12. The clot retrieval device of claim 1, wherein a molded monolithic body defines the plurality of filaments.

13. The clot retrieval device of claim 1, wherein the plurality of filaments define an hourglass shape.

14. The clot retrieval device of claim 1, wherein the plurality of filaments are in slack with the scaffold is in the expanded state.

15. The clot retrieval device of claim 1, wherein:

each of the plurality of filaments has a length measured along the respective filament between the ends, each of the ends of the plurality of filaments are coupled to the scaffold at corresponding first and second locations, the first and second locations being separated by a distance measured directly across the lumen of the scaffold when the scaffold is in the expanded state, and the length of each of the filaments is at least 10% longer than the distance between the first and second locations.

16. The clot retrieval device of claim 1, wherein at least one of the filaments of the plurality of filaments comprises a first portion and a second portion, wherein the first portion extends in a radially outward direction and inverts around the one of the struts or the one of the apices into the second portion, wherein the second portion extends radially inwardly into the lumen.

17. A clot retrieval device, comprising:

a tubular mesh configured to transition between a low-profile state for delivery through a delivery catheter and an expanded state for deployment in a blood vessel at a treatment site proximate a clot, the mesh defining a lumen; and a webbing coupled to the tubular mesh and comprising a plurality of filaments, each spanning the lumen of the mesh, wherein each filament extends between respective ends, wherein each of the ends is coupled to the tubular mesh, wherein, when the device is in the expanded state within the blood vessel at the treatment site, the ends of the filaments lie at a same axial location along the longitudinal axis, wherein the mesh is configured to engage peripheral portions of the clot and the webbing is configured to engage non-peripheral portions of the clot.

18. The clot retrieval device of claim 17, wherein the one or more filaments define a plurality of segments, and wherein in the expanded state each segment extends from the plurality of struts or apices into the lumen.

19. The clot retrieval device of claim 17, wherein the plurality of filaments comprises a first filament and a second filament, and wherein, in the expanded state, the first filament and the second filament cross in a projection onto a plane perpendicular to the longitudinal axis.

20. The clot retrieval device of claim 19, wherein the first filament and the second filament are in contact at a location within the lumen in the expanded state.

* * * * *